United States Patent
Narayan et al.

(10) Patent No.: US 11,433,235 B2
(45) Date of Patent: Sep. 6, 2022

(54) SYSTEMS AND METHODS FOR DELIVERING NON-INVASIVE NEUROMODULATION TO REDUCE THE EFFECTS OF SHOCK AND TRAUMATIC BRAIN INJURY IN ANIMALS AND HUMANS AND TO PROLONG LIFE

(71) Applicant: The Feinstein Institutes for Medical Research, Manhasset, NY (US)

(72) Inventors: Raj Kumar Narayan, Manhasset, NY (US); Chunyan Li, Manhasset, NY (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 0 days.

(21) Appl. No.: 17/045,429

(22) PCT Filed: Apr. 20, 2018

(86) PCT No.: PCT/US2018/028622
§ 371 (c)(1),
(2) Date: Oct. 5, 2020

(87) PCT Pub. No.: WO2019/203850
PCT Pub. Date: Oct. 24, 2019

(65) Prior Publication Data
US 2021/0154474 A1    May 27, 2021

(51) Int. Cl.
*A61N 1/36*    (2006.01)
*A61N 1/05*    (2006.01)

(52) U.S. Cl.
CPC ....... *A61N 1/36031* (2017.08); *A61N 1/0502* (2013.01); *A61N 1/36017* (2013.01); *A61N 1/36034* (2017.08)

(58) Field of Classification Search
CPC .............. A61N 1/36031; A61N 1/0502; A61N 1/36017; A61N 1/36034
See application file for complete search history.

(56) References Cited

U.S. PATENT DOCUMENTS

| 8,729,129 | B2 | 5/2014 | Tracey et al. | |
| 2014/0135886 | A1* | 5/2014 | Cook | A61N 1/36017 607/136 |
| 2017/0354821 | A1* | 12/2017 | Kealey | A61N 1/36114 |
| 2017/0361097 | A1* | 12/2017 | Williamson | A61N 1/36034 |

* cited by examiner

*Primary Examiner* — Amanda K Hulbert
*Assistant Examiner* — Philip C Edwards
(74) *Attorney, Agent, or Firm* — Proskauer Rose LLP

(57) ABSTRACT

Systems and methods of mitigating one or more bodily effects of a shock condition experienced by an animal (including a human, e.g., a patient) are described. One exemplary method includes providing a device for applying non-invasive neurostimulation to the animal's trigeminal nerve. The method also includes applying the non-invasive neurostimulation to the animal's trigeminal nerve, thereby increasing oxygen flow to the animal's brain and/or reducing brain inflammation.

25 Claims, 4 Drawing Sheets

SYSTEMS AND METHODS FOR DELIVERING NON-INVASIVE NEUROMODULATION TO REDUCE THE EFFECTS OF SHOCK AND TRAUMATIC BRAIN INJURY IN ANIMALS AND HUMANS AND TO PROLONG LIFE

CROSS-REFERENCE TO RELATED APPLICATIONS

This application is a National Stage Application under 35 U.S.C. § 371 of International Application No. PCT/US18/28622, filed Apr. 20, 2018, the entire disclosure of which is incorporated herein by reference.

FIELD OF THE INVENTION

In general, the invention relates to systems and methods for non-invasive neurostimulation of animals, including humans. More specifically, the invention relates to systems and methods for non-invasive neurostimulation of an animal's trigeminal nerve to prolong life by mitigating and/or deferring the effects of acute blood loss resulting in hemorrhagic shock (HS) and to improve outcomes from traumatic brain injury.

BACKGROUND OF THE INVENTION

"Shock" is the clinical condition in which a biological tissue's demands for oxygen and nutrients cannot be met by blood flow. For example, in traumatic HS, the failure to meet tissue demands owes to blood loss. Under such circumstances, the brain—the organ most susceptible to low blood flow—is the first to be damaged. Other etiologies of shock can cause similar health problems.

Traumatic HS in particular is a major cause of preventable death after trauma. Approaches to pre-hospital resuscitation strategies to reverse or mitigate the ongoing hemodynamic collapse remain controversial. To date, solutions utilising the trigeminal nerve's link to the body's innate oxygen conserving reflex and pressure response (e.g., via its projection to the rostral ventrolateral medulla (RVLM)) have remained elusive.

SUMMARY OF THE INVENTION

The invention, in various embodiments, features systems and methods for delivering electrical trigeminal nerve stimulation (TNS) to an animal as a novel resuscitation strategy for HS, e.g., to control blood pressure and improve hemodynamic stability during pre-hospital trauma care. In some embodiments, the invention uses closed-loop stimulation to maintain the animal's hemodynamics and/or periods of stimulation being turned "on" or "off" to balance the animal's autonomic nervous system, providing a non-invasive, easy-to-apply, safe solution to improve outcomes.

The trigeminal nerve is the largest cranial nerve and consists of both afferent and efferent fibers. It is divided into three main branches (ophthalmic, maxillary and mandibular) that are connected to the sympathetic (SNS) and parasympathetic (PNS) autonomic nervous systems in the brain. The autonomic nervous system controls most of the body's functions that we do not have voluntary control over—including heart rate, blood pressure and cerebral blood flow. This anatomy is believed to be the basis of the 'diving response'—an intriguing phenomenon seen in mammals such as dolphins and whales that allows them to spend prolonged periods of time underwater.

In the present invention, TNS can modulate both SNS and PNS activities to activate the endogenous pressor response, improve cerebral perfusion and decrease inflammation, leading to reduction of secondary brain injury. This approach has been shown in an animal model to extend the survival time from severe hemorrhage, as discussed below. This approach is unique in that for the first time the body's endogenous protective mechanisms are being employed to ameliorate the adverse consequences of hemorrhagic shock. Such an approach will be a paradigm shift in the way we treat severe hemorrhage, especially in the critical early hours after initial injury.

In one aspect, the invention features a method of mitigating one or more bodily effects of a shock condition experienced by an animal (e.g., a rat or a human). The method includes providing a device for applying non-invasive neurostimulation to the animal's trigeminal nerve. The method also includes applying the non-invasive neurostimulation to the animal's trigeminal nerve using the device, thereby increasing a blood pressure of the animal and an oxygen flow to the animal's brain. The method also improves outcomes from traumatic brain injury by increasing oxygen supply to the animal's brain and by reducing inflammation.

In some embodiments, the method extends a survival time of the animal without resuscitation and/or before resuscitating the animal using traditional methods. In some embodiments, the trigeminal nerve is stimulated by applying the non-invasive neurostimulation to one of the animal's forehead, cheek, nose, tongue, or other facial skin. In some embodiments, applying the non-invasive neurostimulation to the animal's trigeminal nerve includes targeting at least one of the animal's ophthalmic nerve, maxillary nerve, or mandibular nerve to elevate a blood pressure of the animal and improve hemodynamic stability. In some embodiments, applying the non-invasive neurostimulation to the animal's trigeminal nerve is conducted both before and after fluid resuscitation of the animal to improve the animal's hemodynamic stability.

In some embodiments, applying the non-invasive neurostimulation to the animal's trigeminal nerve occurs during acute blood loss (e.g., uncontrolled bleeding). In some embodiments, applying the non-invasive neurostimulation to the animal's trigeminal nerve occurs after acute blood loss (e.g., controlled bleeding). In some embodiments, applying the non-invasive neurostimulation to the animal's trigeminal nerve is conducted to alleviate consequences and progression of HS, traumatic brain injury compounded by hemorrhage, and tissue and/or organ injury compounded by hemorrhage.

In some embodiments, the non-invasive neurostimulation has a frequency of 15-140 Hz. In some embodiments, the non-invasive neurostimulation has an intensity of 2-20 V. In some embodiments, the non-invasive neurostimulation has a duty cycle of 1 second "on" and 1-2 seconds "off". In some embodiments, the non-invasive neurostimulation includes a pulse width of 0.25-1 ms. In some embodiments, intermittent trigeminal nerve stimulation is conducted (e.g., provided to the animal) to maintain augmented hemodynamics achieved during active stimulation while attenuating an overall sympathetic nervous system hyperactivity during a non-stimulation period. In some embodiments, a duration of active stimulation is between 0.5 and 2 minutes. In some embodiments, a duration of non-stimulation duration is between 3 and 20 minutes.

In some embodiments, at least one of a stimulation voltage or a current is increased gradually (e.g., steps of 0.5 V) to reach an elevated systemic and/or systolic blood pressure (e.g., of 5-15 mmHg as compared to a baseline pre-stimulation blood pressure during active stimulation). In some embodiments, at least one of a stimulation voltage or current is modulated to generate low-frequency (e.g., 0.2-1 Hz) oscillatory patterns of systemic blood pressure associated with an increased tolerance to central hypovolemia. In some embodiments, a pulse width is increased up to 1 ms if the maximum stimulation voltage and/or current cannot increase the blood pressure (e.g., during a decompensation phase of hemorrhagic shock).

In some embodiments, closed-loop trigeminal nerve stimulation is conducted. In some embodiments, the closed-loop trigeminal nerve stimulation is conducted based on a systemic or a systolic blood pressure of the animal. In some embodiments, the closed-loop trigeminal nerve stimulation is conducted based on a heart rate of the animal. In some embodiments, the closed-loop trigeminal nerve stimulation is conducted based on a heart rate variability (HRV) of the animal. In some embodiments, certain parameters of the stimulation are modulated to maintain values of the parameters within a target range (e.g., maintaining the blood pressure in the range of 50±5 mmHg, 60±5 mmHg, etc., to have fewer side effects).

In some embodiments, the trigeminal nerve stimulation is conducted simultaneously with small volume or large fluid resuscitation or vasopressors. In some embodiments, the trigeminal nerve stimulation (e.g., for 0.5-2 minutes) is conducted first and followed by a small volume (e.g., 0.5-1 ml in the rat model of hemorrhagic shock) or large volume fluid resuscitation or vasopressors. In some embodiments, a small volume (e.g., 0.5-1 ml in the rat model of hemorrhagic shock) fluid resuscitation is conducted first and followed by the trigeminal nerve stimulation (e.g., for 0.5-2 minutes).

BRIEF DESCRIPTION OF THE DRAWINGS

The advantages of the invention described above, together with further advantages, may be better understood by referring to the following description taken in conjunction with the accompanying drawings. The drawings are not necessarily to scale; emphasis is instead generally placed upon illustrating the principles of the invention.

DETAILED DESCRIPTION

Figure 1B:
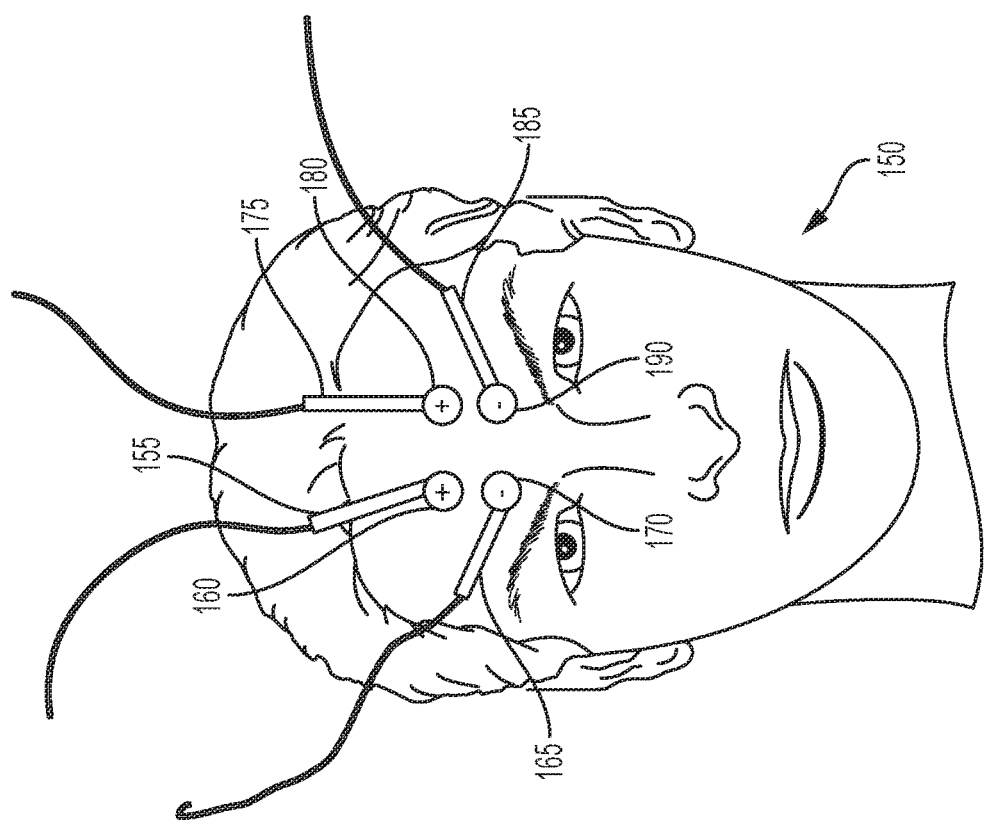
FIG. 1B shows a human patient receiving non-invasive neurostimulation of the trigeminal nerve via targeting of the ophthalmic division using two pairs of electrodes, according to an illustrative embodiment of the invention.
Figure 1A:
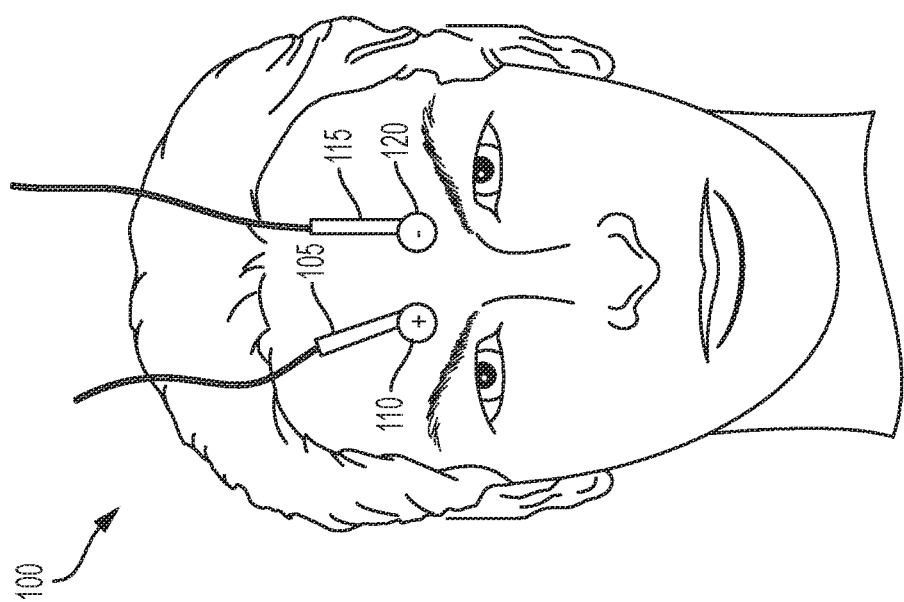
FIG. 1A shows a human patient receiving non-invasive neurostimulation of the trigeminal nerve via targeting of the ophthalmic division using one pair of electrodes, according to an illustrative embodiment of the invention.

FIG. 1A shows a human patient 100 receiving non-invasive neurostimulation of the trigeminal nerve via targeting of the ophthalmic division (the first major division of the trigeminal nerve that supplies the skin over the forehead and around the eyes) using one pair of electrodes, according to an illustrative embodiment of the invention. A first electrode 105 is placed on a first location 110 on the patient's face and a second electrode 115 is placed on a second location 120 on the patient's face. The ophthalmic division is reachable via the first location 110 and the second location 120.

Figure 3:
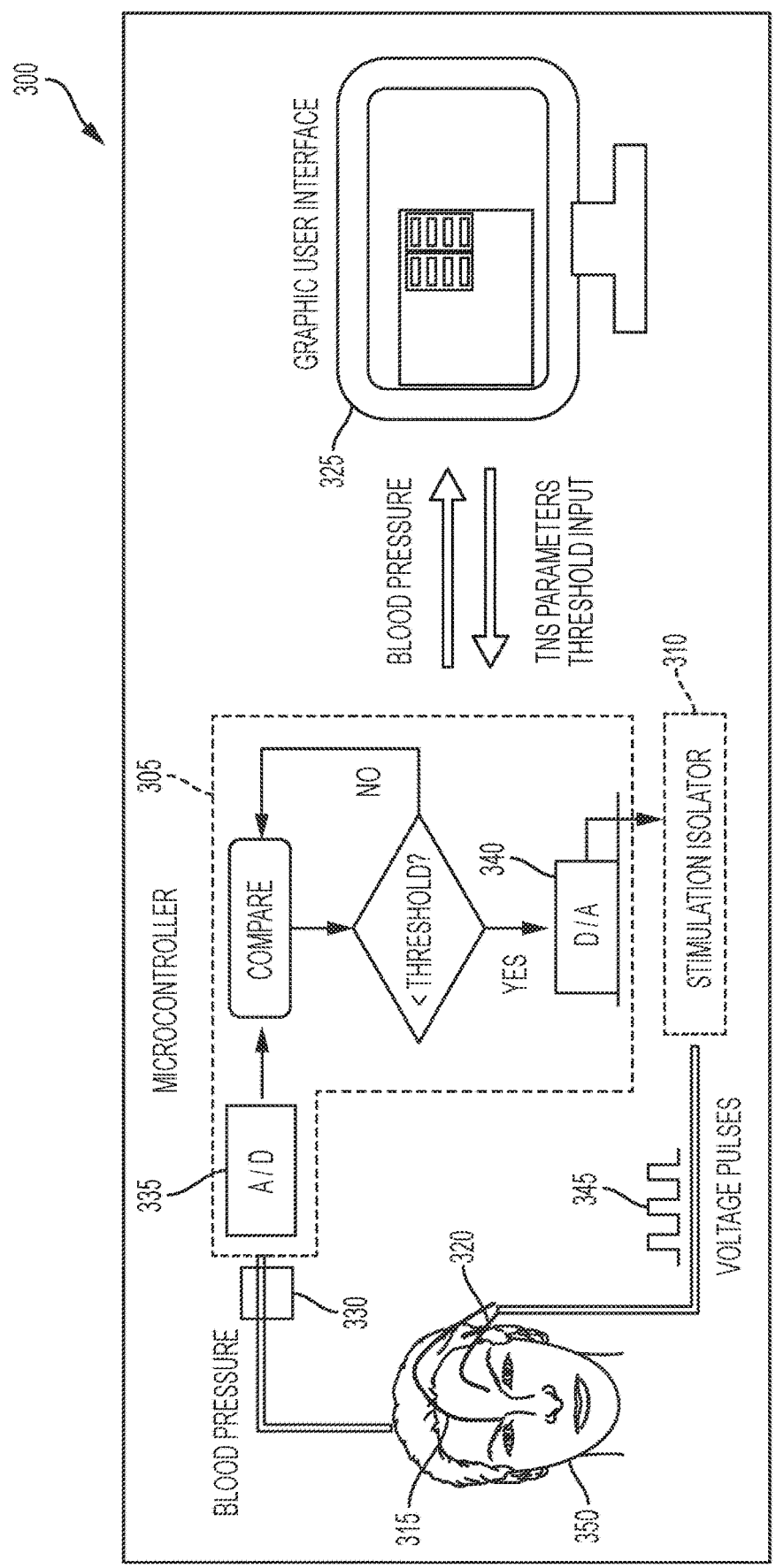
FIG. 3 shows a device for providing non-invasive neurostimulation of the trigeminal nerve using a closed-loop system that reacts to the patient's blood pressure, according to an illustrative embodiment of the invention.

Electrical stimulation of the trigeminal nerve is delivered in the supraorbital or infraorbital region of the face (e.g., using one pair of electrodes, cathode and anode, over the right and left side), using surface stimulation electrodes connected to a constant current/voltage stimulator (e.g., using a device shown and described in FIG. 3 herein). Rectangular-wave pulses (e.g., 0.25-1 ms duration) are delivered for variable durations (e.g., 0.5-2 min) at variable time intervals (e.g., 3-20 min), and stimulus intensity is set to increase the blood pressure by 3-15 mmHg as compared to a baseline blood pressure (pre-stimulation). Electrical stimulation can be provided using, for example, an A-M Systems Model 2100 Isolated Pulse Stimulator (in this setup or others described herein).

FIG. 1B shows a human patient 150 receiving non-invasive neurostimulation of the trigeminal nerve via targeting of the ophthalmic division using two pairs of electrodes, according to an illustrative embodiment of the invention. A first electrode 155 is placed on a first location 160 of the patient's face, and a second electrode 165 is placed on a second location 170 of the patient's face. A third electrode 175 is placed on a third location 180 of the patient's face, and a fourth electrode 185 is placed on a fourth location 190 of the patient's face. The maxillary division is reachable via the first location 160, the second location 170, the third location 180, and the fourth location 190, and is connected to the main trunk of the trigeminal nerve.

Electrical stimulation of the trigeminal nerve is delivered in the supraorbital or infraorbital region of the face (e.g., using two pair of electrodes, cathode and anode, over the right and left branch), using surface stimulation electrodes connected to a constant current/voltage stimulator (e.g., using a device shown and described in FIG. 3 herein). As above, rectangular-wave pulses (e.g., 0.25-1 ms duration) are delivered for variable durations (e.g., 0.5-2 min) at variable time intervals (e.g., 3-20 min), and stimulus intensity is set to increase the blood pressure by 3-15 mmHg as compared to a baseline blood pressure (pre-stimulation). Electrical stimulation can be provided using, for example, an A-M Systems Model 2100 Isolated Pulse Stimulator (in this setup or others described herein).

Figure 2A:
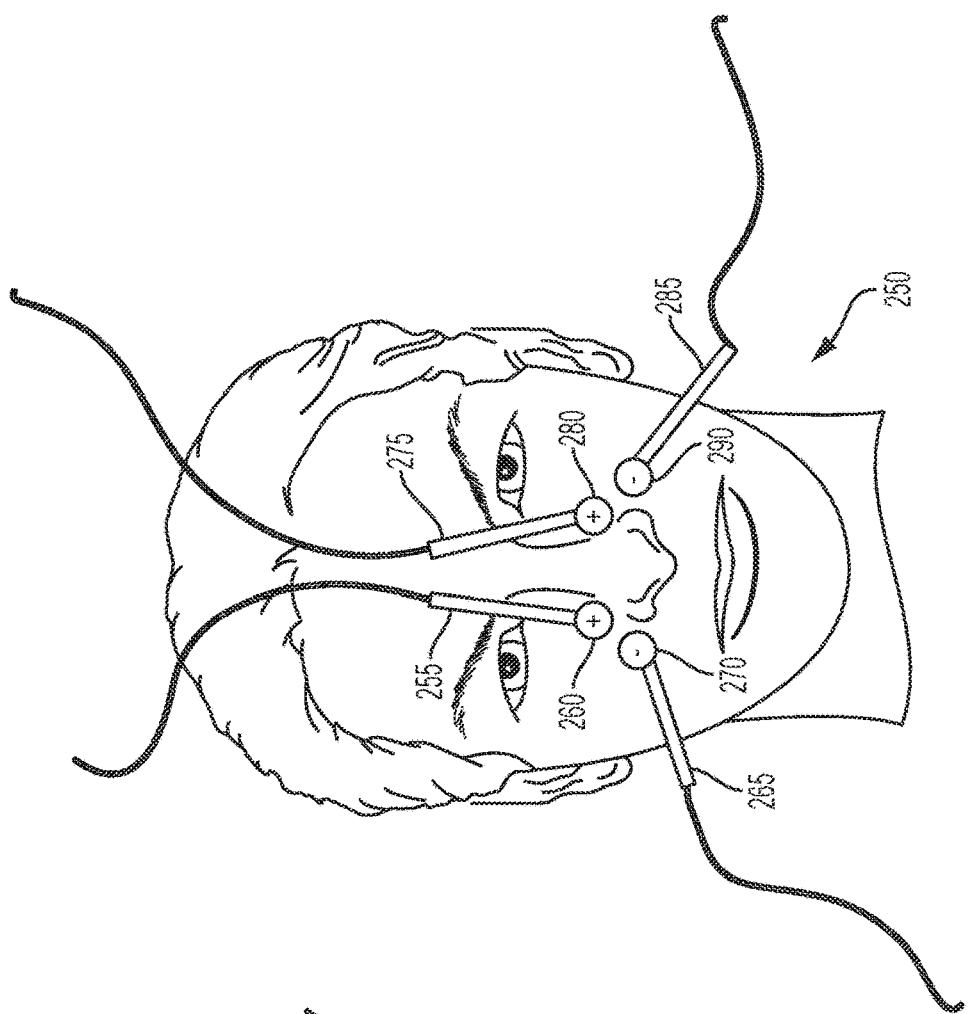
FIG. 2A shows a human patient receiving non-invasive neurostimulation of the trigeminal nerve via targeting of the maxillary division using one pair of electrodes, according to an illustrative embodiment of the invention.

FIG. 2A shows a human patient 200 receiving non-invasive neurostimulation of the trigeminal nerve via targeting of the maxillary division (the second major division of the trigeminal nerve that supplies the skin over the cheeks) using one pair of electrodes, according to an illustrative embodiment of the invention. A first electrode 205 is placed on a first location 210 on the animal's face and a second electrode 215 is placed on a second location 220 on the animal's face. The maxillary division is reachable via the first location 210 and the second location 220 and, like the ophthalmic division, is also connected to the main trunk of the trigeminal nerve.

Electrical stimulation of the trigeminal nerve is delivered via the branches of the ophthalmic division of the trigeminal nerve (e.g., using one pair of electrodes, cathode and anode, over the right and left branch), using surface stimulation electrodes connected to a constant current/voltage stimulator (e.g., using a device shown and described in FIG. 3 herein). Rectangular-wave pulses (0.25-1 ms duration) are delivered for variable durations (0.5-2 min) at variable time intervals (3-20 min), and stimulus intensity is set to increase the blood pressure of 3-15 mmHg as compared to a baseline blood pressure (pre-stimulation).

Figure 2B:
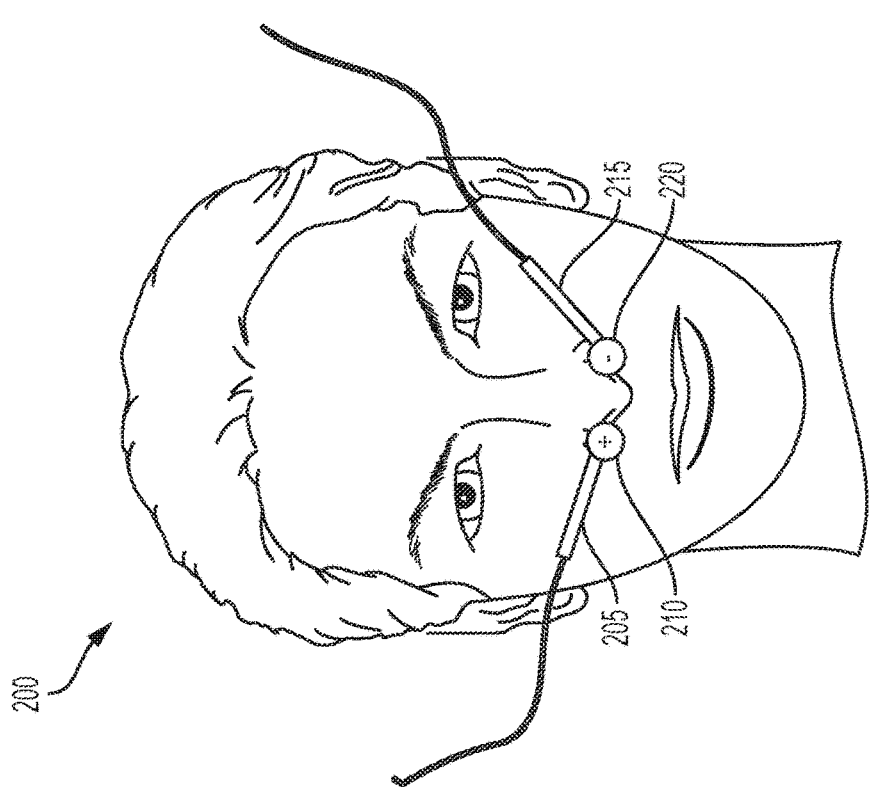
FIG. 2B shows a human patient receiving non-invasive neurostimulation of the trigeminal nerve via targeting of the maxillary division using two pairs of electrodes, according to an illustrative embodiment of the invention.

FIG. 2B shows a human patient 250 receiving non-invasive neurostimulation of the trigeminal nerve via targeting of the maxillary division using two pairs of electrodes, according to an illustrative embodiment of the invention. A first electrode 255 is placed on a first location 260 of the animal's face, and a second electrode 265 is placed on a second location 270 of the animal's face. A third electrode 275 is placed on a third location 280 of the animal's face, and a fourth electrode 285 is placed on a fourth location 290 of the animal's face. The maxillary nerve is reachable via the first location 260, the second location 270, the third location 280, and the fourth location 290, and is connected to the trigeminal nerve.

Electrical stimulation of the trigeminal nerve is delivered via branches of the ophthalmic division of the trigeminal nerve (e.g., using two pairs of electrodes, cathode and anode, over the right and left branch), using surface stimulation electrodes connected to a constant current/voltage stimulator (e.g., using a device shown and described in FIG. 3 herein). Rectangular-wave pulses (0.25-1 ms duration) are delivered for variable durations (0.5-2 min) at variable time intervals (3-20 min), and stimulus intensity is set to increase the blood pressure of 3-15 mmHg as compared to a baseline blood pressure (pre-stimulation).

FIG. 3 shows a device 300 for providing non-invasive neurostimulation of the trigeminal nerve (e.g., according to the methods shown and described above) using a closed-loop system that reacts to the patient's blood pressure, according to an illustrative embodiment of the invention. The device 300 can be an automated closed-loop resuscitation system including a microcontroller 305, a stimulation isolator 310 in electrical communication with the microcontroller 305, electrodes 315, 320 in electrical communication with the stimulation isolator 310, a graphic user interface (GUI) 325 in electrical communication with the microcontroller 305, and a pressure transducer 330 in electrical communication with the microcontroller 305. The microcontroller can include an analog to digital converter (A/D) 335 and a digital to analog (D/A) converter 340. The microcontroller 305 can have circuitry and/or software programming for causing non-invasive trigeminal nerve stimulation to be triggered in the stimulation isolator 310 using a physiologic feedback loop, based on, for example: blood pressure; pulse rate; arterial oxygen saturation; plethysmography; central venous pressure; transcranial doppler; and/or near infrared spectroscopy (e.g., cranial diffusions). In some embodiments, the device can include skin-applied adhesive electrodes.

During operation, the pressure transducer 330 and its analog front-end record arterial pressure of an animal (e.g., a human patient) 350 and send it to the microcontroller 305. The analog to digital converter (A/D) 335 of the microcontroller 305 samples the recorded pressure signal and compares it with a threshold value preset by a user via the GUI 325. When the recorded signal is lower than the threshold, the digital to analog (D/A) converter 340 of the microcontroller 305 sends voltage and/or current pulses with given parameters preset by the GUI 325 to the current stimulation isolator 310 (e.g., amplitude). The stimulation isolator 310 delivers the stimulation voltages 345 to the trigeminal nerve (e.g., via the face) using a stimulation electrode (e.g., 315 or 320). The stimulation on the trigeminal nerve increases the blood pressure until the sampled blood pressure signal is equal to the targeted value. Meanwhile, the microcontroller 305 also transmits the recorded blood pressure signal to the GUI 325 through a universal asynchronous receiver transmitter (UART) known in the art (not shown) for real-time monitoring and reference.

Figure 4:
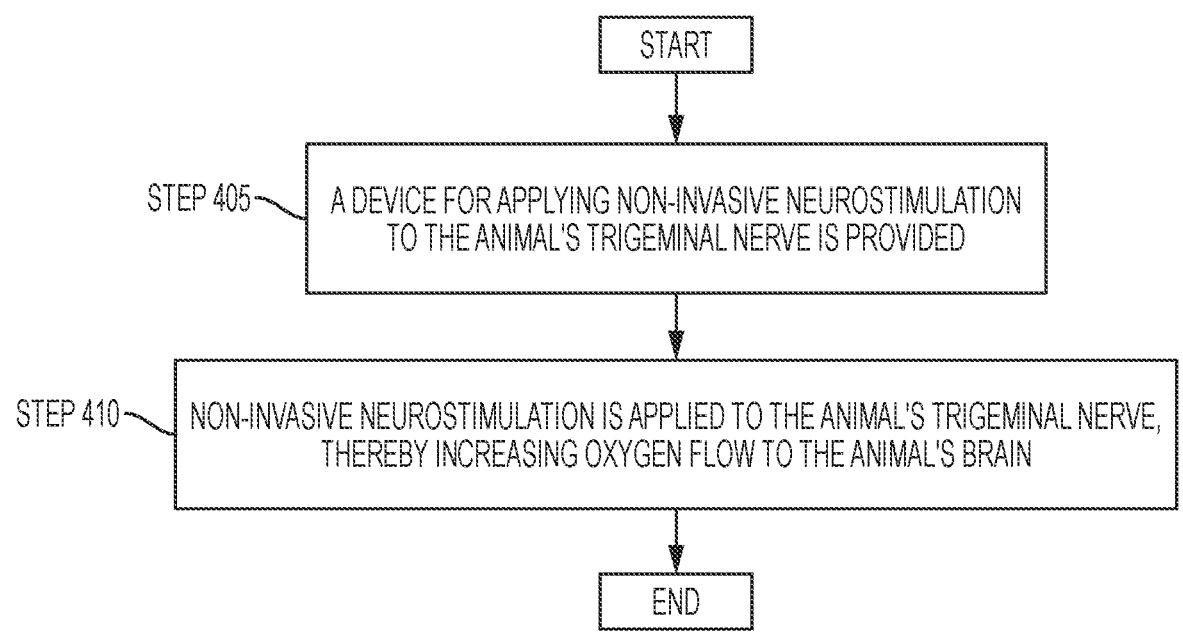
FIG. 4 shows a flow chart of a method for providing non-invasive neurostimulation of an animal's trigeminal nerve, thereby mitigating one or more bodily effects of hemorrhagic shock experienced by an animal, according to an illustrative embodiment of the invention.

FIG. 4 shows a flow chart of a method for providing non-invasive neurostimulation of an animal's trigeminal nerve, thereby mitigating one or more bodily effects (e.g., decreased blood flow to the brain) of hemorrhagic shock (i.e., induced by hypovolemia or acute blood loss) experienced by an animal (e.g., thereby extending a survival time of the animal after the animal has experienced the shock condition), according to an illustrative embodiment of the invention. In a first step 405, a device for applying non-invasive neurostimulation to the animal's trigeminal nerve is provided. In a second step 410, the non-invasive neurostimulation is applied to the animal's trigeminal nerve, thereby increasing oxygen flow to the animal's brain.

Experimental results showing the effectiveness of the above systems and methods have been obtained in male Sprague-Dawley rats. A volume-controlled HS model (50% of the total blood volume removal over 20 minutes) was used to create severe HS in male Sprague-Dawley rats (260-320 grams each). The rats were divided into three groups: sham-animals; HS-animals; and HS-animals with immediate TNS. Electrical stimulation of the rats' trigeminal nerves was performed by introducing two needles (26 GA) subcutaneously and bilaterally along an imaginary line connecting the ear and eye. Rectangular cathodal pulses (0.5 ms) were delivered by an electrical stimulator at 25 Hz and 4V continuously. The 3-hour survival rate, plasma levels of norepinephrine (NE), lactate dehydrogenase (LDH), aminotransferase (AST) and creatinine were quantified using commercially available assay kits according to manufacturer's specifications after 2 hours HS.

The experimental results showed that HS produced significant MAP drops from 115.0±18.7 to 38.3±10.4 mmHg (n=21). Fifteen minutes of TNS after HS increased mean arterial pressure (MAP) from 38.3±10.4 to 68.3±14.2 mmHg (p=0.014; n=17). As compared to HS animals, with TNS, the survival rate was significantly improved (15.4% vs. 64.7%; n=30, p<0.05; HS vs. TNS). TNS also produced significant decreases of organ damages (lactate dehydrogenase (LDH): 155.5±31.0 vs. 42.3±14.6 U/L; Aspartate aminotransferase (AST): 90.9±18.1 vs. 44.3±5.2 IU/L; Creatinine: 0.945±0.007 vs. 0.89±0.06 mg/dl; n=5, p<0.05). After 2-hour HS, plasma norepinephrine (NE) level was decreased after TNS treatment (14.4±3.3 vs. 5.9±2.5 ng/ml; n=4, p<0.05). The evidence presented here, which shows the effectiveness of the invention in targeting the ophthalmic and maxillary nerves to elevate the animal's blood pressure and improve the animal's hemodynamic stability, supports the inference that targeting the mandibular nerve would provide a similarly effective approach.

Thus, the experimental results show that TNS post-blood loss significantly attenuated organ injury and increased survival in an animal model of severe HS. Stimulating the trigeminal nerve may work to mitigate the negative effects of hypovolemic shock by increasing cerebral blood flow and/or blood pressure. Other situations in which similar techniques could prove beneficial include cardiogenic shock (where a myocardial infarction, for instance, diminishes blood flow); anaphylactic shock (where an allergic reaction causes issues with circulation); septic shock (where an overwhelming infection causes widespread mismatch of blood flow); and/or neurogenic shock (caused by damage to the nervous system from a variety of neurological conditions such as spinal cord injury). Trigeminal nerve stimulation can mitigate such effects by ensuring that cerebral blood flow is maintained, and brain damage and/or death can therefore be reduced.

Other circumstances could also be considered. For example, when a cerebral aneurysm ("Berry aneurysm") ruptures and is treated by either surgically or by endovascular techniques (clipping, coiling or stenting), even those patients who survive the initial insult may be at risk of subsequent massive stroke and death from vasospasm. In addition, any brain surgery can cause brain edema and interference with cerebral blood flow. In addition, the invention could find ready application in situations in which brain lesions are treated endovascularly or after ischemic stroke to maximize perfusion.

While the present technological concepts have been particularly shown and described above with reference to exemplary embodiments thereof, it will be understood by those of ordinary skill in the art, that various changes in form and detail can be made without departing from the spirit and scope of the present invention.

What is claimed is:

1. A method of mitigating one or more bodily effects of a shock condition experienced by an animal, the method comprising:
   providing a device for applying non-invasive neurostimulation to the animal's trigeminal nerve; and
   applying the non-invasive neurostimulation to the animal's trigeminal nerve using the device both before and after fluid resuscitation of the animal to improve the animal's hemodynamic stability, thereby increasing a blood pressure of the animal and an oxygen flow to the animal's brain.

2. The method of claim 1 wherein the method extends a survival time of the animal before resuscitating the animal.

3. The method of claim 1 wherein the trigeminal nerve is stimulated by applying the noninvasive neurostimulation to one of the animal's forehead, cheeks, nose, tongue, or other facial skin.

4. The method of claim 1 wherein applying the non-invasive neurostimulation to the animal's trigeminal nerve includes targeting at least one of the animal's ophthalmic division or maxillary division to elevate a blood pressure of the animal and improve hemodynamic stability.

5. The method of claim 1 wherein applying the non-invasive neurostimulation to the animal's trigeminal nerve includes targeting the mandibular nerve to elevate the animal's blood pressure and improve the animal's hemodynamic stability.

6. The method of claim 1 wherein applying the non-invasive neurostimulation to the animal's trigeminal nerve occurs after acute blood loss.

7. The method of claim 1 wherein applying the non-invasive neurostimulation to the animal's trigeminal nerve is conducted to alleviate consequences and progression of hemorrhagic shock, traumatic brain injury compounded by hemorrhage, and tissue and/or organ injury compounded by hemorrhage.

8. The method of claim 1 wherein the non-invasive neurostimulation has a frequency of 15-140 Hz.

9. The method of claim 1 wherein the non-invasive neurostimulation has an intensity of 2-20 V.

10. The method of claim 1 wherein the non-invasive neurostimulation has a duty cycle of 1 second "on" and 1-2 seconds "off".

11. The method of claim 1 wherein the non-invasive neurostimulation includes a pulse width of 0.25-1 ms.

12. The method of claim 1 wherein intermittent trigeminal nerve stimulation is conducted to maintain augmented hemodynamics achieved during active stimulation while attenuating an overall sympathetic nervous system hyperactivity during a non-stimulation period.

13. The method of claim 12 wherein a duration of active stimulation is between 0.5 and 2 minutes.

14. The method of claim 12 wherein a duration of non-stimulation duration is between 3 and 20 minutes.

15. The method of claim 12 wherein at least one of a stimulation voltage or a current is increased gradually to reach an elevated systemic and/or systolic blood pressure of 5-15 mmHg as compared to a baseline blood pressure during active stimulation.

16. The method of claim 12 wherein at least one of a stimulation voltage or current is modulated to generate low-frequency oscillatory patterns of systemic blood pressure associated with an increased tolerance to central hypovolemia.

17. The method of claim 12 wherein a pulse width is increased up to 1 ms if the maximum stimulation voltage and/or current cannot increase the blood pressure.

18. The method of claim 1 wherein closed-loop trigeminal nerve stimulation is conducted.

19. The method of claim 18 wherein the closed-loop trigeminal nerve stimulation is conducted based on a systemic or a systolic blood pressure of the animal.

20. The method of claim 18 wherein the closed-loop trigeminal nerve stimulation is conducted based on a heart rate of the animal.

21. The method of claim 18 wherein the closed-loop trigeminal nerve stimulation is conducted based on a heart rate variability (HRV) of the animal.

22. The method of claim 18 wherein parameters of the stimulation are modulated to maintain values of the parameters within a target range.

23. The method of claim 1 wherein the trigeminal nerve stimulation is conducted simultaneously with small or large volume fluid resuscitation or vasopressors.

24. The method of claim 23 wherein the trigeminal nerve stimulation is conducted first and followed by a small or large volume fluid resuscitation or vasopressors.

25. The method of claim 23 wherein a small volume fluid resuscitation is conducted first and followed by the trigeminal nerve stimulation.

* * * * *

UNITED STATES PATENT AND TRADEMARK OFFICE
CERTIFICATE OF CORRECTION

| | |
|---|---|
| PATENT NO. | : 11,433,235 B2 |
| APPLICATION NO. | : 17/045429 |
| DATED | : September 6, 2022 |
| INVENTOR(S) | : Narayan et al. |

It is certified that error appears in the above-identified patent and that said Letters Patent is hereby corrected as shown below:

In the Specification

At Column 1, Line 16, before the "FIELD OF THE INVENTION", please insert the following paragraph:
-- STATEMENT REGARDING FEDERALLY SPONSORED RESEARCH OR DEVELOPMENT
This invention was made with government support under grant no. W81XWH-18-1-0773 awarded by the Department of Defense. The government has certain rights in the invention. --

Signed and Sealed this
Ninth Day of January, 2024

Katherine Kelly Vidal
*Director of the United States Patent and Trademark Office*